US00PP21246P2

(12) United States Plant Patent
Kordes

(10) Patent No.: US PP21,246 P2
(45) Date of Patent: Aug. 31, 2010

(54) SHRUB ROSE PLANT NAMED 'KORPURLIG'
(50) Latin Name: *Rosa hybrida*
Varietal Denomination: KORpurlig

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/459,096

(22) Filed: Jun. 25, 2009

(51) Int. Cl.
*A01H 5/00* (2006.01)

(52) U.S. Cl. ..... Plt./107

(58) Field of Classification Search ..... Plt./107
See application file for complete search history.

(56) References Cited

OTHER PUBLICATIONS

2008/1246 European Union CVPO summary Aug. 15, 2008 European Union.

*Primary Examiner*—Susan B McCormick Ewoldt

(57) ABSTRACT

A new and distinct variety of rose with long lasting, novel violet pink flowers, and attractive foliage with good disease resistance. It exhibits low growing, spreading growth with abundant flowers. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida*, 'KORpurlig'.

BACKGROUND OF THE INVENTION

The new variety of rose plant of the present invention originated from a controlled crossing made in a rose breeding program between 'KORmixal' a non-patented rose and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpurlig'.

SUMMARY OF THE INVENTION

The new rose plant may be distinguished from its seed parent, 'KORmixal' by the following combination of characteristics:

1. The flower color of the seed parent is red, while the flower color of 'KORpurlig' is violet pink.
2. The petal count of the seed parent is single, while the petal count of KORpurlig is very double.

The new rose plant may be distinguished from its pollen parent, an 'un-named seedling' by the following combination of characteristics:

1. The flower color of the pollen parent is pink, while the flower color of 'KORpurlig' is violet pink.
2. The foliage size of the pollen parent is large, while the foliage size for 'KORpurlig' is small.

The objective of the hybridization was to create a new and distinct rose plant with unique qualities, such as:

1. Spreading growth and flowering;
2. Abundant attractive, recurrent flowers;
3. Attractive and abundant foliage; and 4. Resistance to diseases encountered in landscapes and gardens.

This combination of qualities is not present in prior rose cultivars known to the inventor. These objectives have been substantially achieved and in that distinguish 'KORpurlig' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpurlig' was selected in May, 1999 from the seedling beds to be asexually propagated for further evaluation. The first asexual propagation of 'KORpurlig' was done by budding to seedling understocks in July 1999 at the inventor's nursery in Offenseth-Sparrieshoop, Germany.

This initial and other subsequent propagations conducted in controlled environments demonstrate that 'KORpurlig' reproduces true to type in successive generations of asexual reproduction.

BRIEF DESCRIPTION OF THE DRAWING

The accompanying drawing shows as true as is reasonably possible to obtain in color photographs of this type, the typical characteristics of the buds, flowers, reproductive organs, leaves, and stems of 'KORpurlig'.

DETAILED BOTANICAL DESCRIPTION

The following is a description of 'KORpurlig', as observed growing in October, 2008 in a nursery in Jackson County, Oreg. on plants of two years of age. Color references are made using The Royal Horticultural Society (London, England) Colour Chart, 2001 except where common terms of color are used.

For a comparison, several physical characteristics of the rose variety 'KORsineo', a rose variety from the same inventor described and illustrated in U.S. Plant patent application Ser. No. 20,743 and filed on Aug. 15, 2008 are compared to 'KORpurlig' in Chart 1.

CHART 1

| Characteristic | 'KORpurlig' | 'KORsineo' |
|---|---|---|
| Plant, overall height | 40-50 cm | 60-70 cm |
| Flower petal count | 65-70 petals | 40-45 petals |
| Average leaf size | 95-100 mm (1) × 50-55 mm (w) | 100-105 mm (1) × 50-60 mm (w) |

Parents:

*Seed parent.*—'KORmixal'.

*Pollen parent.*—'un-named seedling'.

Classification:

*Botanical classification.*—*Rosa hybrida,* 'KORpurlig'.

*Commercial classification.*—Shrub.

FLOWER AND FLOWER BUD

Blooming habit: Continuous.

Flower bud:

*Size.*—Upon opening, 18 mm in length from base of receptacle to end of bud and 7 mm diameter at its widest point.

*Bud form.*—Short. Pointed ovoid.

*Bud color.*—As sepals first unfold, bud color is Red Group 53B. When ¼ open, the upper surface of petals is Red-Purple Group N66A and the lower surface is Red-Purple Group 61B.

*Sepals.*—Size: Average 14-15 mm long×4-6 mm wide. Shape: Sepals generally subulate. Sepal apex is generally cirrose. Weak foliaceous appendages on three of the five sepals. Base is flat at union with receptacle. Quantity: Five. Margins: With stipitate glands. Surface texture: Inner side: Covered in fine white hairs. Outer surface: Smooth. Stipitate glands are absent. Color: Upper surface Green Group 143B. Lower surface Green Group 143A. Intonations of Yellow-Green Group 145B.

Receptacle:

*Surface.*—Limited numbers of fine long white hairs.

*Color.*—Yellow-Green Group 144A.

*Shape.*—Urn-shaped.

*Size.*—5-6 mm (h)×4-5 mm (w).

Peduncle:

*Surface.*—With stipitate glands.

*Length.*—25-30 mm average length.

*Diameter.*—1.5-2.0 mm average diameter.

*Color.*—Green Group 143C.

*Strength.*—Weak.

*Borne.*—Multiple buds per stem. Generally, 5-8 buds per flowering stem.

*Anthocyanin.*—Greyed-Purple Group 183A.

Flower bloom:

*Fragrance.*—Moderate.

*Duration.*—On the plant 7 to 8 days. Long lasting. Senesced petals drop away cleanly.

*Size.*—Small flowered garden rose. When open, the average flower diameter is 45-48 mm and the average flower height is 20-22 mm.

*Form.*—Shape of flower when viewed from the side: Upon opening, upper part: Flat. Upon opening, lower part: Flattened convex. Open flower, upper part: Flattened convex. Open flower, lower part: Concave.

Color:

*Upon opening, petals.*—Outermost petals: Outer side: Red-Purple Group 61B. Inner side: Red-Purple Group N66. Innermost petals: Outer side: Red-Purple Group 61B. Inner side: Red-Purple Group N66A.

*Upon opening, basal petal spots.*—Basal petal spot, outermost petals: Outer side: Yellow-Green Group 150D. Inner side: Yellow Group 2D. Basal petal spot, innermost petals: Outer side: Yellow Group 2C. Inner side: Yellow Group 2B.

*After opening, petals.*—Outermost petals: Outer side: Red-Purple Group 61C. Inner side: Red-Purple Group N66A. Innermost petals: Outer side: Red-Purple Group 61B. Inner side: Red-Purple Group N66.

*After opening, basal petal spots.*—Basal petal spot, outermost petals: Outer side: Green-Yellow Group 1D. Inner side: Green-Yellow Group 1D. Basal petal spot, innermost petals: Outer side: Yellow Group 2B. Inner side: Yellow Group 2B.

*Variegations.*—Occasional streak on innermost petals of Green-White Group 157C.

General tonality: On open flower Red-Purple Group N66A. No change in the general tonality at the end of the 7$^{th}$ day. Afterwards, general tonality is Red-Purple Group 67A.

Petals:

*Petal count.*—Approximately 65-70 petals under normal conditions.

*Petal reflex.*—Petals reflex somewhat.

*Petal edge.*—Entire with slight point in center of margin.

*Petal shape.*—Deltoid. Apex shape is round. Shape of base is acute.

*Petal size.*—23-25 mm long; 16-17 mm wide.

*Thickness.*—Average.

*Petal arrangement.*—Generally in a regular pattern with overlapping edges.

Petaloids: Present.

*Petaloid count.*—Average of 15-20 per flower.

*Petaloid edge.*—Smooth.

*Petaloid texture.*—Smooth.

*Petaloid shape.*—Linear to elliptic. Shape of base is acute. Shape of apex is round and ruffled.

*Petaloid size.*—Petaloids are 12 mm long and 7 mm wide.

*Petaloid color.*—Color of inner side is Red-Purple Group N66A. Color of outer side is Red-Purple Group 61C. Occasional streak on inner side of petaloids of Green-White Group 157C.

Reproductive organs:

*Pistils.*—Approximately 25-30 present. Stigmas: Location: Slightly inferior in position to anthers. Color: Green-Yellow Group 1C. Styles: Length: 4 mm long. Color: Greyed-Yellow Group 1D.

*Stamens.*—Approximately 45-50 on average and regularly arranged. Anthers: Size: 2 mm long. Color: Yellow-Orange Group 22A. Pollen: Absent. Filaments: Color: Yellow Group 2B. Length: 6 mm.

THE PLANT

*Plant growth.*—Vigorous, low growing shrub. When grown as a budded nursery plant the average plant height is 40-50 cm and the average plant width is 65-75 cm.

*Stems.*—Stem color: Young wood: Yellow-Green Group 144B. Older Wood: Green Group 137C. Stem surface: Young wood: Smooth. Older wood: Smooth.

*Prickles.*—Present. Incidence: 11-13 per 10 cm of stem. Size: Average length: 5.5 mm. Color: Immature prickles: Greyed-Red Group 181B. Mature prickles: Greyed-Orange Group 164A. Senescing to Greyed-Orange Group 166A. Shape: Concave. Anthocyanin: Color: Greyed-Purple Group 183C.

*Leaves and leaflets.*—Normally 5-7 leaflets on normal leaves in middle of the stem. Leaf size: 95-100 mm (1)×50-55 mm (w). Quantity: Abundant. Texture: Upper side of leaflet: Semi-glossy. Smooth. Under side of leaflet: Matte. Smooth. Thin. Color, mature foliage: Upper leaf surface: Green Group 137A. Lower leaf surface: Green Group 139C. Color, juvenile foliage: Upper leaf surface: Green Group 137A. Lower leaf surface: Green Group 138B. Anthocyanin intonation: Present. Location: Intonations present on juvenile leaf margins, developing leaves, peduncles, rachis, petiole, and stems. Color: Greyed-Purple Group 187B.

*Stipules.*—Size: 15 mm long. 5 mm between the tips of the stipule. Main body of stipule 5-6 mm in width. Shape: Longitudinally flanged or winged along middle. Stipule color: Yellow-Green Group 144A. Anthocyanin: Greyed-Purple Group 184A. Presence of stipitate glands: Present on margins. Margins: With stipitate glands.

*Petiole.*—Length: 10 mm. Diameter: 1.0-1.5 mm. Petiole color: Yellow-Green Group 146B. Anthocyanin present on juvenile tissue, Greyed-Purple Group 187C. Underneath: Smooth. Stipitate glands: Absent.

*Petiole rachis.*—Length: 13-14 mm. Diameter: 1.0-1.5 mm. Color: Yellow-Green Group 146B. Anthocyanin present on juvenile tissue, Greyed-Purple Group 187B. Margins: Very few stipitate glands present. Prickles: Occasional. Stipitate glands: Very few stipitate glands on margins.

*Leaflets.*—Size: Average size of the terminal leaflet is 30 mm (1)×16 mm (w). Shape: Ovate. Base: Ovate. Apex: Acute. Margins: Finely serrated. Texture: Thin.

Hips/seed formation: Color: Green Group 143C with intonations of Greyed- Orange Group N172A and N172B. Size: 9 mm (1)×9 mm (w).

Winter hardiness: To date, the variety has been grown successfully in USDA Hardiness Zone 5.

Disease resistance: Above average resistance to Powdery mildew (*Sphaerotheca pannosa*), rust (*P. disciflorum*), blackspot (*Diplocarpon rosae*), and Botrytis (*Botrytis cinerea*) diseases under normal growing conditions.

I claim:

1. A new and distinct variety of rose plant as herein illustrated and described:

(a) Forms attractive, long lasting violet pink flowers;

(b) Exhibits low growing, spreading habit;

(c) Propagates well using traditional methods, and;

(d) Exhibits very good resistance to disease under normal growing conditions, substantially as herein illustrated and described.

* * * * *

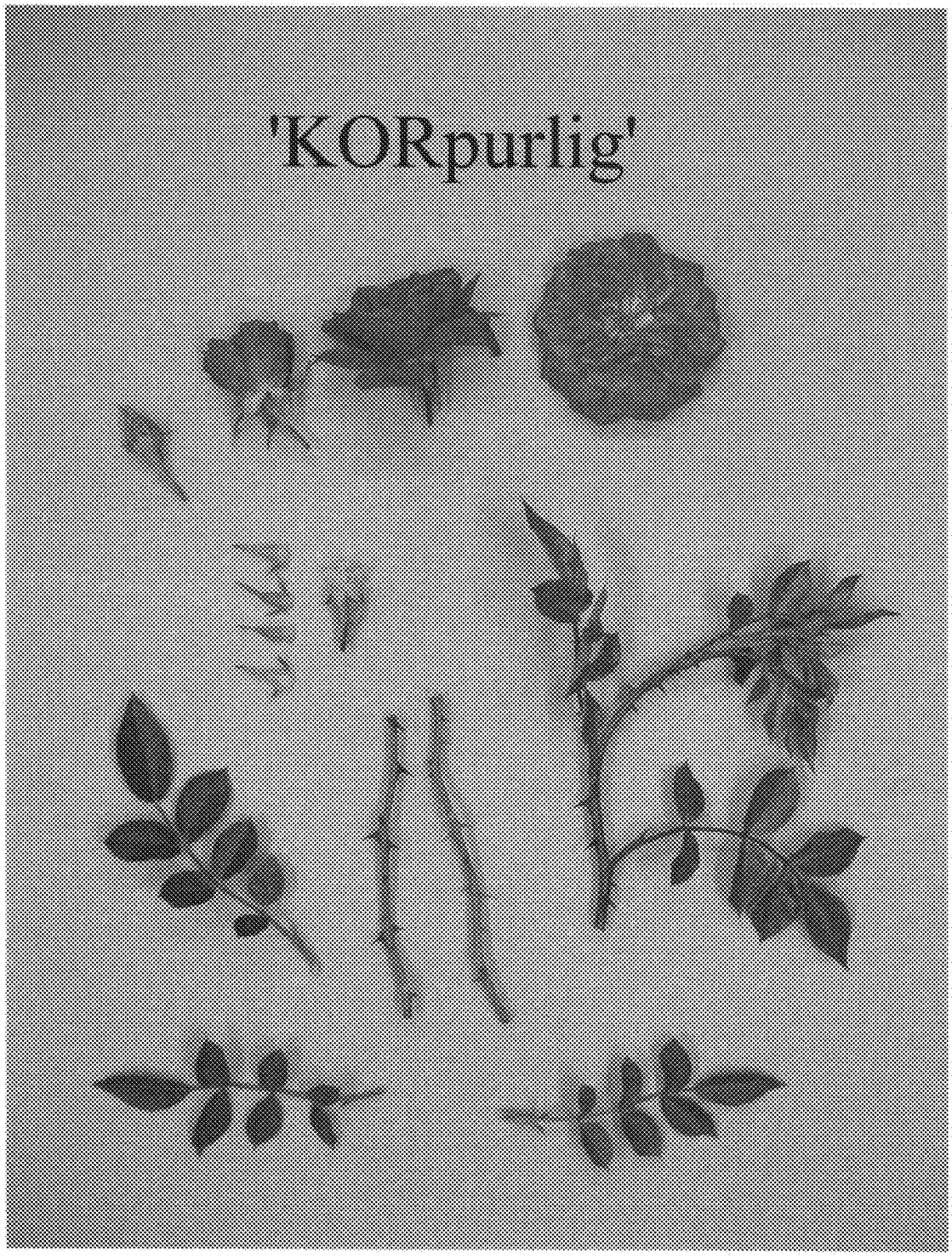
'KORpurlig'